United States Patent [19]
Hon et al.

[11] Patent Number: 6,149,947
[45] Date of Patent: Nov. 21, 2000

[54] COMPOSITIONS OF OAK BARK EXTRACT RELATED SYNTHETIC COMPOSITIONS AND METHOD OF USING SAME

[75] Inventors: David N.-S Hon, Clemson, S.C.; R. Thomas Stanley, Auburndale, Fla.

[73] Assignee: Greystone Medical Group, Inc., Memphis, Tenn.

[21] Appl. No.: 08/947,055

[22] Filed: Oct. 8, 1997

Related U.S. Application Data

[63] Continuation of application No. 08/596,689, Feb. 2, 1996, abandoned, which is a continuation of application No. 08/334,795, Nov. 4, 1994, abandoned, which is a continuation of application No. 07/973,071, Nov. 6, 1992, abandoned.

[51] Int. Cl.[7] .......................... A61K 33/00; A61K 33/06; A61K 33/14; A61K 33/30
[52] U.S. Cl. .......................... 424/641; 424/642; 424/678; 424/679; 424/682; 514/863
[58] Field of Search ................................ 424/195.1, 641, 424/642, 682, 678, 679; 514/863

[56] References Cited

U.S. PATENT DOCUMENTS

| | | | |
|---|---|---|---|
| 37,901 | 3/1863 | Conway | 424/716 |
| 55,911 | 6/1866 | Salie | 424/697 |
| 202,246 | 4/1878 | Delisser | 424/125 |
| 256,847 | 4/1882 | Mayer | 424/197.1 |
| 3,928,584 | 12/1975 | Hudson | 424/195 |
| 4,059,695 | 11/1977 | Hirosaki et al. | 424/195.1 |
| 4,847,083 | 7/1989 | Clark | 424/642 |
| 4,943,432 | 7/1990 | Biener | 424/647 |
| 5,006,551 | 4/1991 | Groke et al. | 514/461 |
| 5,080,900 | 1/1992 | Stanley | 424/195.1 |

FOREIGN PATENT DOCUMENTS

| | | |
|---|---|---|
| 1000950 | 5/1989 | Belgium . |
| 0217975 | 4/1987 | European Pat. Off. . |
| 812341 | 7/1949 | Germany . |
| 819127 | 7/1949 | Germany . |
| 833840 | 7/1949 | Germany . |
| 60164467 | 8/1985 | Japan . |

OTHER PUBLICATIONS

Shani et al., Pharmacological Research Communications, 17:501–512, 1985.
Chase; Dr. Chase's Recipes or Information for Everybody: An Invaluable Collection of About Eight Hundred Practical Recipes, Etc.; 1867; p. 100.
Bencelok Ointment Labels; Circa; 1956 and 1989.
King J. American Dispensatory, 8th Edition, 1870; 691–3.
Steinmetz, E.F.; Codex Vegetabilis, 1957; No. 934, 936, 937; Amsterdam.
The Merck Index; 9th Edition; 1976; No. 7349; Merck & Co. Rahway, New Jersey.

*Primary Examiner*—Jon P. Weber
*Assistant Examiner*—Janet M. Kerr
*Attorney, Agent, or Firm*—King and Schickli, PLLC

[57] ABSTRACT

Higher concentrations of oak bark ash extract, i.e., greater than 20% by weight, are useful for the treatment of skin cancers. Lower concentrations of oak bark extract possess additional therapeutic properties not heretofore recognized. For example, preparations containing 40–80% oak bark extract are useful in the treatment of acute cancerous skin ulcers. In addition, synthetic mixtures containing potassium ions, zinc ions, calcium ions provide many of the same advantageous properties of oak bark extract. The inclusion of rubidium ions and sulfur is also advantageous for some applications.

5 Claims, No Drawings

COMPOSITIONS OF OAK BARK EXTRACT RELATED SYNTHETIC COMPOSITIONS AND METHOD OF USING SAME

This is a continuation of prior application Ser. No. 08/596,689, filed on Feb. 2, 1996 entitled COMPOSITIONS OF OAK BARK EXTRACT RELATED SYNTHETIC COMPOSITIONS, AND METHOD OF USING SAME, now abandoned, which was a continuation of prior application Ser. No. 08/334,795, filed on Nov. 4, 1994 entitled COMPOSITIONS OF OAK BARK EXTRACT RELATED SYNTHETIC COMPOSITIONS, AND METHOD OF USING SAME, now abandoned, which was a continuation of prior application Ser. No. 07/973,071, filed on Nov. 6, 1992 entitled COMPOSITIONS OF OAK BARK EXTRACT RELATED SYNTHETIC COMPOSITIONS, AND METHODS OF USING SAME, now abandoned.

BACKGROUND OF THE INVENTION

This application relates to compositions of aqueous oak bark extract, to synthetic compositions containing the key active ingredients of oak bark extract and to the use of such compositions in the treatment of skin cancer and other skin disorders.

Oak bark extract has been described in U.S. Pat. No. 5,080,900 which is incorporated herein by reference, for use in the treatment of skin ulcers, particularly decubitus ulcers or bed sores. This material in a base of WHITFIELD'S ointment has also been sold under the trade name BENCE-LOK® for use in the treatment of minor skin irritations. The amount of oak bark extract in these materials was relatively low, however. For example, the BENCELOK® preparations have continued from 0.25 to 3% by weight of ash-derived components based upon the total weight of the preparation.

SUMMARY OF THE INVENTION

It has now been found that higher concentrations of oak bark extract possess highly useful properties for the treatment of skin cancers, and that lower concentrations of oak bark extract possess additional therapeutic properties not heretofore recognized. For example, preparations containing 40–80% oak bark extract are useful in the treatment of acute cancerous skin ulcers. In addition, it has now been found that synthetic mixtures containing potassium ions, zinc ions, calcium ions provide many of the same advantageous properties of oak bark extract. The inclusion of rubidium ions and sulfate ions is also advantageous for some applications.

DETAILED DESCRIPTION OF THE INVENTION

Oak bark extract for use in the present invention is prepared from oak bark ash. The bark utilized can be from Red Oak (Quercus rupra L), Black Oak (Quercus velutina Lam.), Shumerd Oak (Quercus shumardi i Buckl.), Scarlet Oak (Quercus coccinea Muenchb.), Willow Oak (Quercus phellos L.) and other species of the Erythrobalanus group. The oak bark is burned to convert it into an ash, which is cooled and screened to provide a powder.

The ash powder is then poured slowly into boiling water and boiled, with stirring, for a period of time (1.5 to 4 hours) to achieve an intermediate oak bark extract. The hot intermediate extract is then filtered to recover a clear filtrate and boiled for an additional period of time to achieve the desired final concentration of oak bark extract. During this boiling step, a white precipitate forms which is separated from the oak bark extract and discarded. Table 1 shows processing conditions which can be used to prepare oak bark extract of various final concentrations. The solution concentrations are expressed as weight percent of oak bark ash derived material.

The oak bark extracts in accordance with the invention are complex mixtures of inorganic materials. Further, as is evident from the results of elemental analysis on the various solutions, (See Table 2) the relative amounts of the constituents vary from one concentration to another. For example, the 40% solutions (i.e., a solutions containing a total of 40% by weight of extracted oak bark materials and 60% by weight water) was found to be highly enriched in rubidium relative to lower concentration solutions.

The therapeutic activity of various constituents of oak bark extract has been analyzed with the result that silicon, strontium, barium, manganese, gallium, zirconium and titanium appear to be unnecessary, while therapeutic efficacy has been found for compositions containing just potassium, zinc and calcium ions, in combination with suitable counterions. Thus, synthetic formulations containing, by weight of inorganic solids, 10 to 80 parts potassium ions, preferably 30 to 50 parts 0.00001 to 20 parts zinc ions, preferably 1 to 10 parts

TABLE I

| Solution (%) | Temperature (° C.) | Processing Time (Hours) |
|---|---|---|
| 0.25 | 98 ± 2 | 1.00 |
| 1.00 | 98 ± 2 | 2.00 |
| 10.00 | 98 ± 2 | 8.00 |
| 20.50 | 98 ± 2 | 12.00 |
| 40.00 | 98 ± 2 | 18.00 |
| 80.00 | 98 ± 2 | 21.00 |

0.01 to 10 parts calcium ions, preferably 1 to 5 parts 0 to 40 parts rubidium ions, preferably 1 to 30 parts, and 0 to 5 parts sulfur, in the form of elemental sulfur or sulfate, together with pharmaceutically acceptable counterions (e.g., $Cl^-$, $SO_4^-$, $CO_3^-$, $OH^-$, $Br^-$). The solution may also contain other inorganic cations, for example, up to 10 parts by weight of inorganic solids of cobalt, copper, iron, manganese, nickel, strontium or aluminum ions, preferably up to 1 part by weight. Further, the composition may include a pharmaceutically acceptable carrier such a water or an ointment or cream base which will result in a therapeutic composition having a pH of from 4 to 7, preferably pH 4.5 to 5.5.

Oak bark extract or the synthetic mixtures of the invention have been found to provide a variety of beneficial therapeutic properties. The therapeutic applications and the concentration of oak bark extract or synthetic mixture by weight of solids are summarized in Table 3.

TABLE 2

| | CONCENTRATION OF OAK BARK EXTRACT | | | | |
|---|---|---|---|---|---|
| Element | 0.25% | 1.00% | 10.00% | 20.50% | 40.00% |
| Hydrogen | 13.77% | 12.07 | 12.15% | 11.00% | 10.11% |
| Oxygen | 86.22% | 87.91 | 85.55% | 84.40% | 64.45% |
| Potassium | 43541 ppm | 0.01% | 2.10% | 4.50% | 25.15% |
| Bromine | 0.05 ppm | 0.07 ppm | 2.00 ppm | 2.02 ppm | 2.02 ppm |
| Calcium | 13.43 ppm | 35.67 ppm | 99.45 ppm | 208.72 ppmp p m | 1000.43 ppm |

TABLE 2-continued

CONCENTRATION OF OAK BARK EXTRACT

| Element | 0.25% | 1.00% | 10.00% | 20.50% | 40.00% |
|---|---|---|---|---|---|
| Chlorine | 24.87 ppm | 45.11 ppm | 92.50 ppm | 185.31 ppm | 235.2 ppm |
| Chromium | 0.23 ppm | 0.55 ppm | 1.01 ppm | 0.49 ppm | 1000.12 ppm |
| Cobalt | ND | ND | 0.08 ppm | 0.16 ppm | 0.29 ppm |
| Copper | ND | ND | 0.11 ppm | 0.33 ppm | 0.68 ppm |
| Iron | ND | ND | 0.85 ppm | 1.70 ppm | 2.12 ppm |
| Lead | ND | ND | 0.23 ppm | 0.56 ppm | 0.3 ppm |
| Manganese | ND | ND | 0.04 ppm | 0.07 ppm | 0.07 ppm |
| Nickel | ND | ND | 0.33 ppm | 0.66 ppm | 2.11 ppm |
| Rubidium | 17.25 ppm | 42.79 ppm | 110.13 ppm | 220.60 ppm | 1320.23 ppm |
| Strontium | ND | 0.01 ppm | 1.79 ppm | 2.99 ppm | 3.3 ppm |
| Sulfur | 5.45 ppm | 30.01 ppm | 180.01 ppm | 373.40 ppm | 421.3 ppm |
| Titanium | 0.81 ppm | 0.24 ppm | 1.79 ppm | 3.44 ppm | 0.1 ppm |
| Zinc | 1.74 ppm | 4.78 ppm | 8.81 ppm | 17.65 ppm | 12.3 ppm |

ND: not detectable.

TABLE III

| Weight % of Oak Bark Extract | Indications |
|---|---|
| 0.25% | Fungal infection, minor infection, insect bites |
| 1.00% | Eczema, minor burns, sunburn, poison oak, poison ivy, poison sumac, wound healing |
| 3.00% | Pyodermas, dermatitis, pruritic dermatoses, eczema, minor burns, sunburn, poison oak, poison ivy, poison sumac, decubitus ulcers, tropical ulcers, wound healing |
| 5.00% | Decubitus, psoriasis |
| 10.00% | Psoriasis, impetigo, Kaposi sarcoma, warts, gangrene, ischemic ulcer, keratosis |
| 20.50% | Precancerous lesions, basal cell epithelioma, squamous cell carcinoma, keratoacanthoma |
| 40.00% | Acute cancerous ulcers |
| 80.00% | Acute cancerous ulcers |

In particular, compositions containing about 20% or more, preferably 30% to 80% and more preferably 40% to 80%, of oak bark extract or a similarly concentrated synthetic mixture according to the invention can be used to treat cancerous and precancerous skin lesions. As used herein, the term cancerous and precancerous skin lesions includes but is not limited to basal cell epithelioma, squamous cell carcinoma, keratoacanthoma.

Compositions according to the invention are also useful for treating abrasions and other partial thickness wounds. Useful compositions include at least potassium, zinc and calcium ions and may include other ionic components as well as described in Examples 1 and 2. The composition is advantageously applied in a cream or ointment base over a period of several days. Similar compositions were found to be useful in the treatment of gangrene, impetigo, psoriasis, although longer periods of treatment may be required.

While not intending to be bound by any particular mechanism of action, it appears that oak bark extract and synthetic mixtures containing the key ingredients of oak bark extract function to enhance wound healing by providing complexing ions which interact with enzymes such as alkaline phosphatase, carbonic anhydrase, carboxypeptidase, various enhydrogenases, arginase, carnosinase, dehydropeptidase, glycine dipeptidase, histidine deaminase and tripeptidase, oxyloacetic carboxylase, and some lecithinases and enolases. These enzymes are involved in numerous biosynthetic pathways necessary for wound healing, for example, collagen biosynthesis, and are believed to function with greater efficiency in the presence of the complexing ions.

The application will now be further described by way of the following, non-limiting examples.

EXAMPLE 1

A synthetic mixture is prepared by combining zinc sulfate (2.5 g), calcium hydroxide (2 g), potassium carbonate (3.5 g) and rubidium hydroxide (6 g), potassium hydroxide (6 g) in distilled water (80 g) and WHITFIELD'S ointment (57 g). The total amount of synthetic chemicals is 3% in weight. This formulation is used to treat lacerations. The laceration is cleaned with rubbing alcohol and air dried. The ointment is applied to the laceration twice daily, to provide reduced redness with 4 hours and healing with 72 hours.

EXAMPLE 2

A synthetic mixture is prepared by combining potassium hydroxide (6.6 g), rubidium hydroxide (0.4 g), zinc sulfate (0.6 g), sulfur (2 g) and calcium hydroxide (0.1 g) in distilled water (14.55 g) and WHITFIELD'S ointment (72.75 g). The total amount of synthetic chemicals is 10% in weight. This formulation is used to treat psoriasis. The psoriasis is cleaned with rubbing alcohol to remove any contamination. The ointment is applied twice daily until healed.

EXAMPLE 3

A synthetic mixture is prepared by combining potassium hydroxide (6.6 g), rubidium hydroxide (0.4 g), zinc sulfate (0.6 g), sulfur (2 g) and calcium hydroxide (0.1 g) in distilled water (14.55 g) and WHITFIELD'S ointment (72.75 g). The total amount of synthetic chemicals is 10% in weight. This formulation is used to treat impetigo. The affected area is thoroughly cleaned with rubbing alcohol to remove any contamination. The ointment is applied to impetigo twice daily until healed.

EXAMPLE 4

A synthetic mixture is prepared by combining potassium hydroxide (6.6 g), rubidium hydroxide (0.4 g), zinc sulfate (0.6 g), sulfur (2 g) and calcium hydroxide (0.1 g) in distilled water (14.55 g) and WHITFIELD'S ointment (72.75 g). The total amount of synthetic chemicals is 10% in weight. This formulation is used to treat gangrene. The gangrene was thoroughly cleaned with hydrogen peroxide to remove any contamination. The ointment is applied to gangrene twice daily until healed.

EXAMPLE 5

Five additional synthetic compositions are prepared as follows:

(a) Potassium carbonate (10 g), rubidium hydroxide (4 g), zinc sulfate (2.5 g), calcium hydroxide (3.5 g), distilled water (80 g), WHITFIELD'S ointment (57 g).

(b) Potassium hydroxide (10 g), rubidium hydroxide (4 g), zinc sulfate (2.5 g), calcium hydroxide (3.5 g), distilled water (80 g), WHITFIELD'S ointment (57 g).

(c) Potassium carbonate (12 g), rubidium hydroxide (5.5 g), zinc oxide (2.5 g), distilled water (80 g), distilled water (80 g), WHITFIELD'S ointment (57 g).

(d) Potassium carbonate (12 g), rubidium hydroxide (5.5 g), zinc sulfate (2.5 g) distilled water (80 g), WHITFIELD'S ointment (57 g).

(e) Calcium hydroxide (12 g), rubidium hydroxide (5.5 g), zinc sulfate (2.5 g), distilled water (80 g), WHITFIELD'S ointment (57 g).

We claim:

1. A composition, comprising:

a pharmaceutically acceptable carrier; and an active ingredient of inorganic solids comprising 10–80 parts by weight of potassium ions, 0.00001–20 parts by weight of zinc ions, 0.01–10 parts by weight of calcium ions and 1–40 parts by weight of rubidium ions, said parts by weight being expressed as parts by weight of inorganic solids.

2. The composition according to claim 1 wherein the rubidium ions comprise 1–30 parts by weight of the inorganic solids.

3. The composition according to claim 1, wherein said carrier is water.

4. The composition according to claim 1, wherein said carrier is cream based.

5. A method for treating a skin lesion comprising applying to the lesion an effective amount of a therapeutic composition comprising:

a pharmaceutically acceptable carrier; and an active ingredient of inorganic solids comprising 10–80 parts by weight of potassium ions, 0.00001–20 parts by weight of zinc ions, 0.01–10 parts by weight of calcium ions and 1–40 parts by weight of rubidium ions, said parts by weight being expressed as parts by weight of inorganic solids.

* * * * *